(12) United States Patent
Friesen et al.

(10) Patent No.: US 7,604,954 B2
(45) Date of Patent: Oct. 20, 2009

(54) METHOD FOR EVALUATING KIDNEY FUNCTION IN A FELINE

(75) Inventors: Kim Gene Friesen, Topeka, KS (US); Ryan Michael Yamka, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 370 days.

(21) Appl. No.: 11/617,015

(22) Filed: Dec. 28, 2006

(65) Prior Publication Data

US 2007/0202545 A1 Aug. 30, 2007

Related U.S. Application Data

(60) Provisional application No. 60/754,506, filed on Dec. 28, 2005.

(51) Int. Cl.
*G01N 33/53* (2006.01)
(52) U.S. Cl. .................. 435/7.21; 435/7.1; 435/41; 436/501; 436/543; 530/300; 530/350
(58) Field of Classification Search .................. None
See application file for complete search history.

(56) References Cited

FOREIGN PATENT DOCUMENTS

WO WO 2005/094200 A2 10/2005

OTHER PUBLICATIONS

Ida et al. (Domestic Animal Endocrinology, vol. 32, pp. 93-105, 2007).*
Yoshimoto et al. (Journal of American Society of Nephrology, vol. 13, No. 11, pp. 2748-2752, 2002).*
Guebre-Egziabher et al. (Journal of Renal Nutrition, vol. 15, No. 1, Jan. 2005, pp. 116-120).*
Gale, Susan M., et al., "Energy Homeostasis, Obesity and Eating Disorders: Recent Advances in Endocrinology", The Journal of Nutrition, 134:295-298; 2004.
Guebre-Egziabher, Fitsum, et al., "Leptin, Adiponectin, and Ghrelin Dysregulation in Chronic Kidney Disease" Journal of Renal Nutrition, 15:116-120; 2005.
Akihiro Yoshimoto et al.,"Plasma Ghrelin and Desacyl Ghrelin Concentrations in Renal Failure", *Journal of the American Society of Nephrology*, Williams and Wilkins, Baltimore, MD, vol. 13, No. 11, Nov. 2002, pp. 2748-2752. XP002390260.

* cited by examiner

*Primary Examiner*—Lisa V Cook
(74) *Attorney, Agent, or Firm*—Shannon McGarrah

(57) ABSTRACT

Methods for (1) evaluating feline kidney function by determining ghrelin level in feline tissue or biofluid and correlating the ghrelin level directly to kidney function and (2) diagnosing kidney disease in a feline comprises determining an observed ghrelin level in a tissue or biofluid of the feline and comparing the observed ghrelin level to a reference ghrelin level indicative of normal kidney function, wherein an observed level lower than the reference level is indicative of kidney disease or susceptibility thereto.

13 Claims, No Drawings

METHOD FOR EVALUATING KIDNEY FUNCTION IN A FELINE

CROSS-REFERENCE TO PRIOR APPLICATIONS

This application claims priority from U.S. Provisional Application No. 60/754,506 filed on Dec. 28, 2005.

BACKGROUND OF THE INVENTION

1. Field of the Invention

The present invention relates to methods for evaluating kidney function in felines and methods for diagnosing kidney disease in felines. The invention further relates to kits and communicating means useful in practicing methods of the invention.

2. Description of the Art

Feline kidney disease is the second leading cause of feline death. Possible causes of feline kidney disease include congenital disorders (a feline being born with one kidney or an impaired kidney), kidney infection (resulting from an untreated urethra blockage), decreased blood supply to renal arteries (caused by, for example, diabetes, renal blockage, tumors, or arterial collapse), toxic chemicals, glomerulonephritis, interstitial nephritis, feline leukemia virus infection, feline infectious peritonitis, high blood pressure and renal tumors.

Because the reserve capacity of a kidney is large, kidney disease can progress undetected for a long time, and by the time external signs of the disease are visible, 60% to 75% of the renal mass may already be lost.

Though feline kidney disease is progressive and fatal, early diagnosis can allow the disease to be effectively managed for some time. Thus, there remains a need for new methods for evaluating kidney function and methods for diagnosing kidney disease in felines.

Ghrelin is a peptide hormone produced by endocrine cells in the placenta, kidney, pituitary and hypothalamus and by epithelial cells lining the fundus of the stomach. Initially synthesized as a preprohormone, ghrelin is proteolytically processed to a 28-amino acid peptide.

Ghrelin stimulates growth hormone secretion and regulates energy balance. In rodents and humans, ghrelin increases hunger through activation of hypothalamic feeding centers. Ghrelin secretion is up-regulated under conditions of negative energy balance and down-regulated under conditions of positive energy balance. In humans, dogs and rodents, ghrelin blood levels are reported to increase as kidney function decreases. This is not unexpected as declining kidney function indicates low energy and thus a need for increased food intake. The increase in blood ghrelin levels in these species acts to enhance appetite and in turn, increases food ingestion.

SUMMARY OF THE INVENTION

Surprisingly, it has now been found that in felines, serum ghrelin levels are directly, as opposed to inversely, correlated with certain indicators of kidney function such as blood urea nitrogen (BUN).

Accordingly there is now provided a method for evaluating feline kidney function, comprising determining a ghrelin level in a tissue or biofluid of a feline, and directly correlating the ghrelin level to kidney function.

The invention also provides a method for diagnosing kidney disease in a feline, comprising determining an observed ghrelin level in a tissue or biofluid of the feline, and comparing the observed ghrelin level to a reference ghrelin level indicative of normal kidney function, wherein an observed level lower than the reference level is indicative of kidney disease or susceptibility thereto.

The invention still further provides a method for detecting onset of kidney disease in a feline, comprising monitoring ghrelin level in a tissue or biofluid of the feline over a time period; wherein onset is detected if, at any time point, the ghrelin level exhibits a decrease versus an initial level indicative of healthy kidney function.

The invention further provides a method for selecting a regimen for a feline, comprising (a) determining a ghrelin level in a tissue or biofluid of the feline; (b) evaluating kidney function by direct correlation thereof with the ghrelin level; and (c) identifying a regimen appropriate to the kidney function.

The invention still further provides a method for assessing efficacy of a regimen for managing kidney function in a feline, comprising (a) establishing a baseline ghrelin level in a tissue or biofluid of the feline prior to initiation of the regimen; (b) monitoring observed ghrelin level at least at one time point after initiation of the regimen; and (c) comparing the observed level to the baseline level; wherein maintenance or increase in the observed level relative to the baseline level is indicative of efficacy of the regimen.

There is now also provided a diagnostic kit comprising (a) one or more test materials for determining observed ghrelin levels in a tissue or biofluid of a feline; and (b) one or more user-accessible media carrying information that comprises (i) a reference ghrelin level appropriate to the feline; and (ii) an algorithm that directly correlates an observed ghrelin level, relative to the reference level, to kidney function or that inversely correlates an observed ghrelin level, relative to the reference level, to presence of or susceptibility to kidney disease.

There is still further provided a means for communicating information about direct correlation of kidney function to ghrelin level in a feline, comprising one or more of a product label, a package insert, a brochure, a handout, an advertisement, a public announcement, an audiotape, a videotape, a DVD, a CD-ROM, a computer readable chip, card or disk, a computer memory or a web page.

DETAILED DESCRIPTION OF THE INVENTION

In felines, as in other animals, diminished kidney function is indicated by elevated levels of BUN, creatinine, and BUN to creatinine ratio. It has now been found in domestic cats that increased levels of BUN, or increased BUN to creatinine ratio, correspond to decreased levels of ghrelin. As BUN is a known indicator of diminished kidney function, it can be concluded that ghrelin levels are directly correlated with kidney function in cats. This finding is surprising and contrary to expectations based upon observations of ghrelin levels in other species.

The methods of the invention are useful for felines, including for example, domesticated cats. Other animals belonging to the family Felidae are also included as "felines" herein, such as lions, tigers, jaguars, and other wild and domestic cats.

Kidneys have multiple functions including filtering waste products from the body (primarily urea and creatinine), regulating serum electrolyte levels (potassium, calcium, phosphorus and sodium), producing erythropoietin (which stimulates the bone marrow to produce red blood cells), producing renin (an enzyme that controls blood pressure), and producing and concentrating urine. Impaired kidney function can indicate chronic or acute kidney disease. Acute kidney diseases include, but are not limited to, urinary obstruction, infectious disease, physical injury, and poisoning. Chronic kidney diseases include but are not limited to chronic renal failure, chronic tubulo-interstitial nephritis, glomerulonephritis, pyelonephritis, amyloidosis, hydronephrosis, renal lymphoma, polycystic kidney disease, renal aplasia, renal hypoplasia, renal dysplasia and kidney disease caused by congenital disorders.

The term "kidney disease" herein includes any kidney dysfunction or disorder regardless of whether it is generally recognized as a disease or syndrome.

A method of the invention for evaluating feline kidney function comprises determining a ghrelin level in a tissue or biofluid of a feline, and directly correlating the ghrelin level to kidney function.

The step of directly correlating as used herein is characterized as identifying a level of kidney function consistent with the ghrelin level using a direct correlation between ghrelin level and kidney function. For example, high levels of ghrelin can indicate normal kidney function while low levels of ghrelin can indicate impaired kidney function.

Any tissue or biofluid can be used to determine ghrelin levels. Generally, tissues or biofluids that can be obtained with minimal invasion are more desirable. A biosample, for example, is any sample of a tissue or biofluid used to determine ghrelin levels that is obtained from a live animal. Alternatively, ghrelin levels can be determined in situ without the need to obtain a biosample. Tissues can include but are not limited to bone, muscle, kidney, liver, etc. Biofluids illustratively include whole blood, blood serum, blood plasma, cerebrospinal fluid, crevicular fluid, milk, urine, lymph fluid, intramuscular fluid, nasal secretion and saliva.

A biosample can be collected, for example, at a point of care facility, i.e., a place where an animal can be seen by a health care practitioner (e.g., veterinarian, veterinary technician, etc.) for evaluation and diagnosis. Alternatively, a biosample can be collected at the animal's home, farm, stable, kennel or cattery where the animal is kept.

When a biosample is taken at a single time point, the sample will typically be taken when the feline is in a fasted state, for example, a preprandial (immediately before a meal) time point. However, a biosample can be obtained at any stage of the feline's feeding cycle, for example preprandial or at a suitable interval after a meal (postprandial). When a biosample is taken at more than one time point, the biosample is typically obtained at a consistent stage of the feeding cycle, most conveniently when the feline is in a fasted state. However, a biosample can be obtained at each of a plurality of time points during a feeding cycle, including at least one preprandial time point and at least one postprandial time point.

Ghrelin level from a biosample obtained from a feline can be determined at the place, e.g. point of care facility, where the biosample is taken. A kit as described herein can optionally be used in determining the ghrelin level. Alternatively, the biosample can be sent to a secondary facility. The term "secondary facility" herein refers to a laboratory such as a commercial testing laboratory where clinical samples are evaluated, and can be off-site (i.e., at a different location) from a point of care facility.

In some embodiments, either or both steps of determining a ghrelin level and directly correlating the ghrelin level to kidney function are performed at a point of care facility or a secondary facility.

Ghrelin levels can be determined using assays known in the art. An assay can include any commercially available or non-commercially available assay. Typically, an assay is chosen based on the type of tissue or biofluid in which the ghrelin level is to be determined. For example, a commercially available monoclonal-based immunoassay utilizing monoclonal antibodies reactive to one or more epitopes on the ghrelin molecule can be used to determine a blood serum level of ghrelin.

In some embodiments, ghrelin levels are determined using one or more of enzyme immunoassay, enzyme-linked immunosorbent assay, immunofluorescent assay, radioimmunoassay, western blot assay, biochemical assay, enzymatic assay or calorimetric assay techniques. A variety of labels and conjugation techniques are known by those skilled in the art and can be used in various assays.

Ghrelin level in a sample can be unadjusted, or adjusted for body weight of the feline. An unadjusted level can be expressed in weight/volume concentration units such as mg/l, μg/l or ng/l, or molar concentration units such as μmol/l, nmol/l or pmol/l. An adjusted level can be expressed in similar units, but with body weight (BW) as a divisor, e.g., mg/l/kg BW, pmol/l/kg BW, etc.

The invention also provides a method for diagnosing kidney disease in a feline, comprising determining an observed ghrelin level in a tissue or biofluid of the feline, and comparing the observed ghrelin level to a reference ghrelin level indicative of normal kidney function, wherein an observed level lower than the reference level is indicative of kidney disease or susceptibility thereto.

An "observed ghrelin level" herein is the ghrelin level determined from a tissue or biofluid from a feline in which a diagnosis is to be made.

The reference ghrelin level is generally indicative of normal kidney function. The reference level can be established from one or more biosamples obtained from one or more felines with normal kidney function. Typically, reference levels are established for felines of the same breed or breed type. It is further desirable that the reference levels are established for felines of particular age groups and/or for each sex. The reference ghrelin level can also be established from publicly available documentary data, for example a ghrelin value published in the literature or a norm based on documentary data.

In some embodiments, the reference ghrelin level can be obtained from a database accessible to a professional making the diagnosis.

In some embodiments, the observed ghrelin level is determined in a first feline and the reference ghrelin level is determined in a second feline, wherein the second feline has normal kidney function.

In other embodiments, the observed and reference ghrelin levels are determined in the same feline at different time points. For example, the first time point can establish a baseline or reference level for ghrelin. Ghrelin levels determined at one or more subsequent time points can be considered observed ghrelin levels. The observed and reference ghrelin levels are determined in biosamples obtained at time points that are generally at least about 4 hours apart, for example, at least about 8 hours apart, at least about 12 hours apart, at least about 24 hours apart, at least about 3 days apart, at least about 7 days apart, or at least about 1 month apart.

In some embodiments, an observed ghrelin level lower than the reference level is indicative of kidney disease. In other embodiments, an observed ghrelin level lower than the reference level is indicative of susceptibility to kidney disease. Illustratively, an observed ghrelin level of at least about 10%, at least about 15%, at least about 20%, at least about 25% or at least about 30% lower than the reference ghrelin level is indicative of kidney disease or susceptibility thereto. In general, a greater difference between the reference level and the observed level is indicative of a greater depression of kidney function or a more severe state of kidney disease.

Kidney disease normally progresses over time, initially without detection and/or management by the feline's caregiver. By the time kidney disease is outwardly apparent, kidney function is already greatly diminished. If, however, kidney disease is detected at its onset or a feline is identified as having a predisposition to kidney disease, the animal's health can be managed to minimize the impact of disease.

The invention provides a method for detecting onset of kidney disease in a feline, comprising monitoring ghrelin level in a tissue or biofluid of the feline over a time period; wherein onset is detected if, at any time point, the ghrelin level exhibits a decrease versus an initial level indicative of healthy kidney function.

According to this method, ghrelin levels in a feline are monitored over some period of time, and onset of kidney disease is detected if, at any time point during that period, the ghrelin level decreases relative to the initial ghrelin level. The decrease can be, but is not necessarily, statistically significant.

Monitoring of ghrelin level can be performed at any convenient internal, for example, about hourly, twice daily, daily, twice weekly, weekly, monthly, bimonthly, twice yearly or yearly intervals.

The invention further provides a method for selecting a regimen for a feline, comprising (a) determining a ghrelin level in a tissue or biofluid of the feline; (b) evaluating kidney function by direct correlation thereof with the ghrelin level; and (c) identifying a regimen appropriate to the kidney function.

One embodiment optionally includes the further step of (d) directing a caregiver of the feline to adopt the regimen so identified. Such an embodiment can be considered a method for prescribing a regimen for a feline.

A regimen appropriate to the kidney function can be selected by the feline's caregiver based on information communicated by any suitable communication means, or can be prescribed or suggested by a health care professional. The regimen can comprise dietary or pharmaceutical intervention or both.

Dietary intervention can be by way of providing a composition for consumption by the feline. The composition has nutrient levels appropriate to the kidney function evaluated. Illustratively, such a composition can be a nutritional composition, such as a food composition, a supplement, a treat or a toy, it being noted that some, but not all, supplements, treats and toys are themselves food compositions. Food compositions can be, for example, ingested by an animal or administered to an animal by feeding. The composition useful herein is typically one that is nutritionally adapted for feeding to a feline having healthy or impaired kidney function. The food composition can be particularly adapted to the special nutritional needs of felines of particular breeds, ages, sex. etc. The composition can be available with or without a prescription.

Pharmaceutical intervention appropriate to kidney function can comprise administering to the feline at least one renal drug according to a therapeutically effective regimen. For example, such a renal drug can be selected from ACE inhibitors, endothelin inhibitors, vasopeptide inhibitors, calcium channel blockers, H2 receptor antagonists, proton pump inhibitors, cytoprotectives, antiemetics, androgens, erythropoietin, phosphate binders, calcitriol, and combinations thereof.

The regimen can be continued at a frequency or for a period of time as is necessary or appropriate for the kidney function, whether healthy or impaired. Illustratively, a regimen can continue for at least about 1 month, at least about 2 months, at least about 6 months, at least about 1 year, or for some other period of time as determined necessary or appropriate by, for example, a veterinarian or other health care professional.

The invention still further provides a method for assessing efficacy of a regimen for managing kidney function in a feline, comprising (a) establishing a baseline ghrelin level in a tissue or biofluid of the feline prior to initiation of the regimen; (b) monitoring observed ghrelin level at least at one time point after initiation of the regimen; and (c) comparing the observed level to the baseline level; wherein maintenance or increase in the observed level relative to the baseline level is indicative of efficacy of the regimen.

The baseline ghrelin level is established before starting the feline on a particular regimen. Then, as described above, the ghrelin level is monitored at one or more time points subsequent to initiation of the regimen. The observed ghrelin level(s) relative to the baseline ghrelin level can be individually or collectively indicative of efficacy of the regimen in managing kidney function. For example, maintenance of or increase in the observed ghrelin level relative to the baseline level is indicative of the efficacy of the regimen.

There is also provided a diagnostic kit comprising (a) one or more test materials for determining observed ghrelin levels in a biosample obtained from a feline; and (b) one or more user-accessible media carrying information that comprises (i) a reference ghrelin level appropriate to the feline; and (ii) an algorithm that directly correlates an observed ghrelin level, relative to the reference level, to kidney function or that inversely correlates an observed ghrelin level, relative to the reference level, to presence of or susceptibility to kidney disease. As in previous embodiments, an observed level lower than the reference level is indicative of kidney disease or susceptibility thereto.

"User-accessible" media herein include all media, such as paper, disk, memory chip, card, computer or network, on which instructions, information, an algorithm and/or data can be retrievable contained or stored. The algorithm is typically a software algorithm.

The kit is optionally self-contained so as not to require laboratory equipment, Optionally, the kit further comprises a biosample collection device. The kit can employ one or more of a variety of assays for determining a ghrelin level, including the assays listed above. Standards and standard additions can be included and used for calibration in quantifying the level of ghrelin in a biosample.

In some embodiments, the one or more test materials can comprise one or more reagents. In other embodiments, the one or more test materials of the kit can comprise at least one antibody, for example a polyclonal or monoclonal antibody against ghrelin. The antibody can be immobilized on a solid support. For example, an ELISA can be utilized to determine a level of ghrelin in a sample. The ELISA can involve coupling an antibody onto a solid support such as a polymer. A sample comprising ghrelin can be introduced and allowed to interact with the antibody, whereupon a signal (e.g., chromogenic signal) generating process can be performed to create an optically detectable signal.

In one embodiment, the kit comprises a first antibody that specifically binds to the ghrelin in the sample, and a second antibody that specifically binds to the resulting complex of the first antibody and the ghrelin. The second antibody can be immobilized to a solid support. For example, upon binding of the second antibody to the first antibody/ghrelin complex, the second antibody can trigger a reaction and, for example, result in a detectable color change.

The diagnostic kit can further comprise a means for communicating information about or instructions for (a) evaluating kidney function or diagnosing kidney disease in a feline or (b) a suggested or prescribed regimen appropriate to the kidney function or disease as discussed above.

The communicating means can be attached to or enclosed in a package containing other elements of the kit. Any suitable form of communicating means can be employed, for example a document such as a label, brochure, advertisement or package insert, a computer-readable digital or optical medium such as a diskette or CD, an audio presentation, for example on an audiotape or CD, or a visual presentation, for example on a videotape or DVD. The communicating means can refer to further information located elsewhere, such as on a website.

In a still further embodiment, there is provided a means for communicating information about direct correlation of kidney function to ghrelin level in a feline, comprising one or more of a product label, a package insert, a brochure, a handout, an advertisement, a public announcement, an audiotape, a videotape, a DVD, a CD-ROM, a computer readable chip, card or disk, a computer memory or a web page.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

EXAMPLE

The invention can be further illustrated by the following examples of preferred embodiments thereof, although it will be understood that these examples are included merely for purposes of illustration and are not intended to limit the scope of the invention unless otherwise specifically indicated. The example takes the form of a study illustrating that levels of ghrelin, relative to a reference ghrelin level, can be indicative of kidney function and kidney disease, or susceptibility thereto.

Prior to the study, 40 cats are fed the same food containing sufficient nutrients to meet minimum nutritional requirements. The cats show no sign of renal disease. At the start of the study, cats are split into four groups of 10 cats each and each group is assigned one of four commercially available cat foods. The cats are fed their assigned food daily for 30 days. Cats are given fresh food daily and given access to the food for a period of 20 hours.

Blood is drawn and urine collected at day zero and day 30. Ghrelin and BUN levels are determined in serum and microalbuminuria is determined in urine using conventional methods. Microalbuminuria is performed via Heska ERD Kit. Ghrelin analysis utilizes ELISA. Creatinine and BUN are in the routine chemistry screen analysis. Table 1 shows blood metabolites and urine specific gravity measured at day 30.

TABLE 1

Levels of Blood and Urine Indicators of Kidney Function at Day 30 of Study

|  | Food 1 | Food 2 | Food 3 | Food 4 |
|---|---|---|---|---|
| Serum ghrelin, ng/ml | 1.65 | 1.66 | 1.96 | 1.46 |
| BUN, mg/dl | 20.94 | 22.61 | 19.86 | 26.13 |
| Blood creatinine, mg/dl | 1.07 | 1.18 | 1.08 | 1.03 |
| BUN to creatinine ratio | 19.6 | 19.18 | 19.15 | 29.27 |
| Urine specific gravity | 1.041 | 1.034 | 1.037 | 1.048 |
| Microalbuminuria, mg/dl | 0 | 0.8 | 0.4 | 0.325 |

Each of the four foods contain different concentrations of various nutrients and lead to different outcomes in terms of kidney function as shown at least by BUN levels. The results indicate that low levels of ghrelin are surprisingly associated with high levels of BUN, known to be an indicator of impaired kidney function.

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method for evaluating feline kidney function comprising determining an observed ghrelin level in a tissue or biofluid of a feline and directly correlating the ghrelin level to kidney function by comparing the observed ghrelin level to a reference ghrelin level indicative of normal kidney function, wherein an observed level lower than the reference level is indicative of kidney disease or susceptibility thereto.

2. The method of claim 1 wherein the feline is a cat.

3. The method of claim 1 wherein the tissue or biofluid comprises a biosample obtained from the feline.

4. The method of claim 3 wherein the biosample comprises whole blood, blood plasma, or blood serum.

5. The method of claim 3 wherein the biosample is obtained when the feline is in a fasted state.

6. The method of claim 3 wherein the ghrelin level in the biosample is determined using an assay selected from the group consisting of enzyme immunoassay, enzyme-linked immunosorbent assay, immunofluorescent assay, radioimmunoassay, western blot assay, biochemical assay, enzymatic assay, and calorimetric assay techniques.

7. A method for diagnosing kidney disease in a feline comprising determining an observed gtuelin level in a tissue or biofluid of the feline and comparing the observed ghrelin level to a reference ghrelin level indicative of normal kidney function, wherein an observed level lower than the reference level is indicative of kidney disease or susceptibility thereto.

8. The method of claim 7 wherein the reference ghrelin level represents a norm based on documentary data.

9. The method of claim 7 wherein the observed ghrelin level is determined in a first feline and the reference ghrelin level is determined in a second feline having normal kidney function.

10. The method of claim 7 wherein an observed ghrelin level at least about 10% lower than the reference ghrelin level is indicative of kidney disease or susceptibility thereto.

11. The method of claim 7 wherein the observed and reference ghrelin levels are determined in the same feline at different time points.

12. The method of claim 11 wherein the observed and reference ghrelin levels are determined at time points at least about 4 hours apart.

13. The method of claim 11 wherein the observed and reference ghrelin levels are determined at time points at least about 7 days apart.

* * * * *